United States Patent [19]

Torii et al.

[11] Patent Number: 4,898,939
[45] Date of Patent: Feb. 6, 1990

[54] PROCESS FOR PREPARING 2β-SUBSTITUTED-METHYLPENICILLIN DERIVATIVES

[75] Inventors: Sigeru Torii; Hideo Tanaka; Motoaki Tanaka, all of Okayama; Shozo Yamada, Honjyo; Akira Nakai, Okayama, all of Japan

[73] Assignees: Taiho Pharmaceutical Co., Ltd., Tokyo; Otsuka Kagaku Kabushiki Kaisha, Osaka, both of Japan

[21] Appl. No.: 316,632

[22] Filed: Feb. 28, 1989

[30] Foreign Application Priority Data

Mar. 1, 1988 [JP] Japan .................................. 63-49038

[51] Int. Cl.$^4$ ........................................... C07D 499/00
[52] U.S. Cl. .................................................... 540/310
[58] Field of Search .................. 540/310; 514/192, 193

[56] References Cited

U.S. PATENT DOCUMENTS

| | | | |
|---|---|---|---|
| 4,482,565 | 11/1984 | Fogler et al. | 540/310 |
| 4,496,484 | 1/1985 | Micetich et al. | 260/245.2 |
| 4,529,592 | 7/1985 | Micetich et al. | 424/114 |
| 4,562,073 | 12/1985 | Micetich et al. | 424/114 |
| 4,668,514 | 5/1987 | Micetich | 540/310 |

FOREIGN PATENT DOCUMENTS 62-294686 12/1987 Japan .

OTHER PUBLICATIONS

Synthesis 1986, 292 published in Apr. 1986 and authored by Micetich et al, Tetrahedron Letters, No. 38, pp. 3303–3306 (1975).

Primary Examiner—Nicholas S. Rizzo
Attorney, Agent, or Firm—Armstrong, Nikaido, Marmelstein, Kubovcik & Murray

[57] ABSTRACT

A process for preparing a 2β-substituted-methylpenicillin compound of the formula

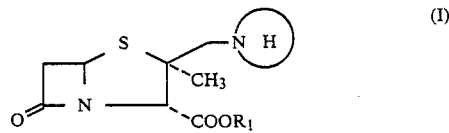 (I)

wherein —N Y is an optionally substituted heterocyclic group containing 2 to 4 nitrogen atoms as the hetero atom in the ring structure, and $R_1$ is a penicillin carboxyl protecting group, the process comprising reacting an azetidinonedisulfide compound of the formula

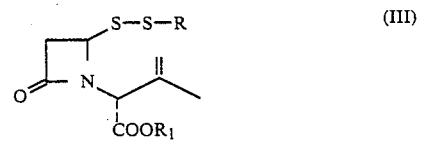 (III)

wherein $R_1$ is as defined above and R is a substituted or unsubstituted heterocyclic group with a nitrogen-containing heterocyclic compound of the formula

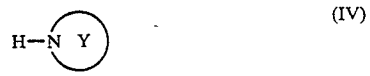 (IV)

wherein

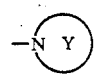

is as defined above in the presence of a metal compound.

9 Claims, No Drawings

PROCESS FOR PREPARING 2β-SUBSTITUTED-METHYLPENICILLIN DERIVATIVES

The present invention relates to a novel process for preparing a 2β-substituted-methylpenicillin derivative and more particularly to a process for preparing a 2β-substituted-methylpenicillin derivative by introducing a nitrogen-containing heterocyclic group to the 2β-methyl group.

The 2β-substituted-methylpenicillin derivative produced by the process of the invention is represented by the formula

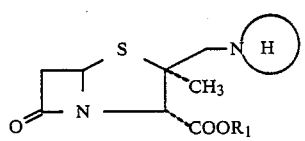
(I)

wherein

is an optionally substituted heterocyclic group containing 2 to 4 nitrogen atoms as the hetero atom in the ring structure, and $R_1$ is a penicillin carboxyl protecting group.

The compound of the formula (I) is useful as the intermediate for preparing a 2β-substituted-methyl-penicillin 1,1-dioxide compound having a potent β-lactamase inhibitory activity and represented by the formula

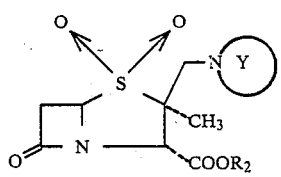
(II)

wherein

is as defined above and $R_2$ is a hydrogen atom or a penicillin carboxyl protecting group that can be readily metabolized or hydrolyzed in vivo to give a free carboxyl group.

Of the compounds of the formula (II), those wherein

is an optionally substituted 1,2,3-triazol-1-yl group are known and processes for preparing such compounds are disclosed in U.S. Pat. Nos. 4,529,592, 4,562,073, 4,668,514 and J. Med. Chem., Vol. 30, 1469 (1987). The disclosed processes are conducted in the following manner.

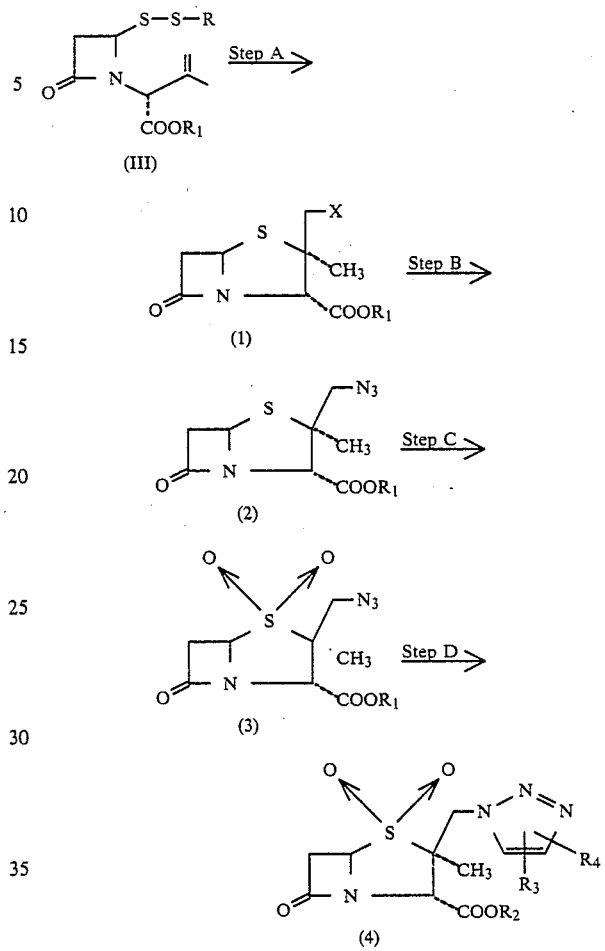

In the foregoing formulas, R is a substituted or unsubstituted heterocyclic group, $R_1$ and $R_2$ are as defined above, $R_3$ and $R_4$ are various substituents such as those disclosed in the foregoing U.S. patents and X is a halogen atom.

In the foregoing reaction scheme, the azetidinoedisulfide compound (III) is converted in step A to a 2β-halogenomethylpenicillin compound (1), which is then converted to an azide compound (2) in step B. The azide compound (2) is then oxidized in step C to give an azide 1,1-dioxide compound (3), which is further reacted in step D with an acetylene derivative which can react with the compound (3) to give a compound (4) having a substituted or unsubstituted 1,2,3-triazol-1-yl group.

However, said process for preparing 1,2,3-triazol-1-yl componds (4) is useful only for introducing substituted or unsubstituted 1,2,3-triazol-1-yl groups and is not useful for introducing various other types of heterocyclic group to the 2β-methyl group of the penicillin derivatives. Furthermore, the above process has the disadvantage of necessitating a number of reaction steps and giving the desired compound in a low yield. Additionally, the process invariably forms as an intermediate the 2β-halogenomethylpenicillin compound (1) which is not stable and requires a cumbersome handling, and also requires the use of azide compound and acetylene derivative which have the danger of explosion and therefore should be used in small amounts with due safety measure. Thus the above prior art process is not commercially advantageous.

An object of the invention is to provide a commercially advantageous process by which a wide variety of heterocyclic groups can be introduced into the 2β-methyl group of penicillin compounds with a minimal number of reaction steps and without necessitating the use of dangerous reactants.

This invention provides a process for preparing a 2β-substituted-methylpenicillin derivative represented by the formula

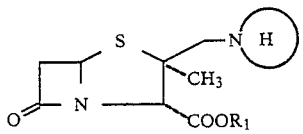
(I)

wherein

is an optionally substituted heterocyclic group containing 2 to 4 nitrogen atoms as the hetero atom in the ring structure, and R₁ is a penicillin carboxyl protecting group, the process comprising reacting an azetidinonedisulfide compond of the formula

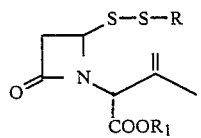
(III)

wherein R₁ is as defined above and R is a substituted or unsubstituted heterocyclic group with a nitrogen-containing heterocyclic compound of the formula

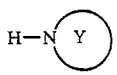
(IV)

wherein

is as defined above in the presence of a metal compound.

We have conducted an intensive research on the reaction of an azetidinone derivative and a nitrogen-containing heterocyclic compound. As the result, we found a versatile process capable of introducing various types of heterocyclic groups selectively into the 2β-methyl group of penicillin derivatives. The present invention has been accomplished based thereon.

The process of the invention requires only one step to produce the compound of the formula (I), which in turn can be easily oxidized, thereby producing the above β-lactamase inhibitory compound of the formula (II) in a good yield. The process of the invention can be conducted with simple procedure without requiring the use of dangerous reactants, and hence is commercially advantageous.

Penicillin carboxyl protecting groups represented by R₁ include known carboxyl protecting groups which are conventionally used in the synthesis of penicillins, and examples thereof are described in Japanese Unexamined Patent Publication No. 49-81380 and in "Cephalosporins and Penicillins, Chemistry and Biology" edited by H. E. Flynn published in 1972 by Academic Press. Preferable examples of the group R₁ are methyl, ethyl, propyl, butyl, tert-butyl, 1,1-dimethylpropyl, 1-cyclopropylmethyl, 2-cyano-1,1-dimethylethyl, bromobenzoylmethyl, p-nitrobenzoylmethyl, dimethylaminomethyl, methylthiomethyl, phenylthiomethyl, succinimidomethyl, trichloroethyl, tribromoethyl, 1,1-dimethyl-2-propenyl, 1,3-dimethyl-3-butenyl, benzyl, diphenylmethyl, trityl, p-nitrobenzyl, p-methoxybenzyl, di(p-methoxyphenyl)methyl, acetoxymethyl, acetoxyethyl, propionyloxyethyl, pivaloyloxymethyl, pivaloyloxyethyl, pivaloyloxypropyl, benzoyloxymethyl, benzoyloxyethyl, benzylcarbonyloxymethyl, cyclohexylcarbonyloxymethyl, methoxymethyl, ethoxymethyl, benzyloxymethyl, 3-phthalidyl, crotonolacton-4-yl, tetrahydropyranyl, dimethylchlorosilyl, trichlorosilyl, pyridine-1-oxide-2-methyl, quinoline-1-oxide-2-methyl and the like.

The heterocyclic group represented by R is a substituted or unsubstituted 5- or 6-membered heterocyclic group which contains 1 to 4 nitrogen atoms and may further contain one oxygen or sulfur atom as the heteroatom in the ring structure and which may optionally be fused with a benzene ring. Examples of the 5- or 6-membered heterocyclic group include pyrrolidinyl, piperazinyl, piperidyl, pyrrolyl, pyridyl, pyrimidyl, imidazolyl, quinolyl, isoquinolyl, benzimidazolyl, benzothiazolyl, benzoxazolyl, thiazolyl, thiadiazolyl, thiatriazolyl, oxazolyl, oxadiazolyl, oxatriazolyl, triazolyl, tetrazolyl and the like. These heterocyclic groups may optionally have 1 to 3 substituents. The substituents include C₁–C₄ alkyl groups such as methyl, ethyl, propyl and butyl, C₁–C₄ alkoxy groups such as methoxy, ethoxy, propoxy and butoxy, halogen atoms such as fluorine, chlorine and bromine, nitro, aryl groups such as phenyl, tolyl and xylyl, aralkyl groups such as benzyl, phenethyl and trityl. Preferable examples of the heterocyclic group represented by R are benzothiazol-2-yl, 2-quinolyl, 2-pyridyl, 3-pyridyl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 1-methylimidazol-2-yl, 1-methylbenzimidazol-2-yl, benzoxazol-2-yl, 1-methyltetrazol-5-yl, 5-methyl-1,3,4-thiadiazol-2-yl, 4-methylthiazol-2-yl and the like, among which the most preferred is benzothiazol-2-yl.

Examples of optionally substituted heterocyclic groups containing 2 to 4 nitrogen atoms as the heteroatom in the ring structure and represented by

are substituted or unsubstituted monocyclic or bicyclic heterocyclic groups only containing 2–4 nitrogen atoms as the hetero atom in the ring structure, such as pyrazolyl, imidazolyl, 1,2,3-triazolyl, 1,2,4-triazolyl, tetrazolyl, benzotriazolyl, benzpyrazolyl, benzimidazolyl and the like. Preferable examples thereof are pyrazol-1-yl, imidazol-1-yl, 1,2,3-triazol-1-yl, 1,2,3-triazol-2-yl, 1,2,4-triazol-1-yl, 1,2,4-triazol-4-yl, tetrazol-1-yl, tetrazol-2-yl, benzotriazol-1-yl, benzpyrazol-1-yl, benzimidazol- 1-yl and the like. These heterocyclic groups may optionally have 1 to 3 substituents, which include $C_1$-$C_6$ straight- or branched-chain alkyl groups such as methyl, ethyl, propyl, isopropyl, butyl, sec-butyl, tert-butyl, pentyl, and hexyl; $C_1$-$C_6$ straight- or branched-chain alkoxy groups such as methoxy, ethoxy, propoxy, butoxy and tert-butoxy; $C_2$-$C_6$ acyl groups such as acetyl, propionyl and butyryl; carbamoyl group; $C_1$-$C_6$ alkyl-substituted carbamoyl groups such as methylcarbamoyl, ethylcarbamoyl, propylcarbamoyl, butylcarbamoyl, pentylcarbamoyl, isopropylcarbamoyl and tert-butylcarbamoyl; halogen atoms such as fluorine, chlorine, bromine and iodine; hydroxyl group; trifluoromethyl group; nitro group; amino group; formyl group; $C_1$-$C_6$ alkoxy-$C_1$-$C_6$ alkyl groups such as methoxymethyl, ethoxymethyl, propyloxymethyl, butoxymethyl, methoxyethyl, ethoxyethyl, propyloxyethyl and butoxyethyl; $C_2$-$C_7$ alkoxycarbonyl groups such as methoxycarbonyl, ethoxycarbonyl, propyloxycarbonyl, isopropyloxycarbonyl, butoxycarbonyl, sec-butoxycarbonyl, tert-butoxycarbonyl, pentyloxycarbonyl and hexyloxycarbonyl; $C_3$-$C_7$ alkenyloxycarbonyl groups such as 1-propenyloxycarbonyl and 1-butenyloxycarbonyl; benzyloxycarbonyl groups which may optionally have 1-3 substituents selected from the group consisting of $C_1$-$C_6$ alkyl group, a halogen atom such as fluorine, chlorine or bromine and nitro group on the benzene ring, such as benzyloxycarbonyl, o-nitrobenzyloxycarbonyl, p-nitrobenzyloxycarbonyl, m-nitrobenzyloxycarbonyl, p-chlorobenzyloxycarbonyl, m-chlorobenzyloxycarbonyl, o-fluorobenzyloxycarbonyl, p-bromobenzyloxycarbonyl, o-methylbenzyloxycarbonyl, p-ethylbenzyloxycarbonyl, m-propylbenzyloxycarbonyl, 4-nitro-2-ethylbenzyloxycarbonyl, 2,4-dinitrobenzyloxycarbonyl, 2,4,6-trinitrobenzyloxycarbonyl, 2,4-dimethylbenzyloxycarbonyl and 2,4,6-triethylbenzyloxycarbonyl; phenyl groups which may optionally have 1-3 substituents selected from the group consisting of $C_1$-$C_6$ alkyl group, $C_1$-$C_6$ alkoxy group and a halogen atom including fluorine, chlorine or bromine on the benzene ring, such as phenyl, tolyl, xylyl, 2-ethylphenyl, 4-ethylphenyl, 2,4,6-trimethylphenyl, 2-methoxyphenyl, 4-methoxyphenyl, 2,4-dimethoxyphenyl, 4-chlorophenyl, 4-bromophenyl, 2,4-dichlorophenyl, 4-fluorophenyl and 4-bromophenyl; $C_1$-$C_6$ alkyl groups substituted with 1-3 phenyl groups such as benzyl, phenylethyl, diphenylmethyl and trityl; $C_1$-$C_6$ alkylthio groups such as methylthio, ethylthio, propylthio and isopropylthio; $C_1$-$C_6$ alkylsulfinyl groups such as methylsulfinyl, ethylsulfinyl, propylsulfinyl and isopropylsulfinyl; $C_1$-$C_6$ alkylsulfonyl groups such as methylsulfonyl, ethylsulfonyl, propylsulfonyl and isopropylsulfonyl and the like.

The compounds of the formula (III) used as the starting material in the process of the invention are known and described, for example, in U.S Pat. No. 4,518,533, Japanese Unexamined Patent Publications No. 60-243064 and No. 62-242660 and can be prepared by known processes disclosed in these publications.

The metal compound useful in the process of the invention includes various salts or oxides of heavy metals such as silver, cerium, copper, lead, mercury, thallium and the like. Preferable examples of the heavy metal salts are heavy metal salts of an organic carboxylic acid, especially $C_2$-$C_4$ fatty acid such as acetic acid, and include copper acetate, lead acetate, silver acetate, mercury (I) acetate, mercury (II) acetate, cerium acetate and the like. Also usable as the salt are carbonates of such heavy metals, such as silver carbonate, copper carbonate and the like. Preferable examples of the oxides of heavy metals are mercury oxide, copper oxide, lead oxide, silver oxide and the like. It is important to conduct the reaction in the presence of the metal compound. If the metal compound is not used, the desired compound of the formula (I) can not be obtained.

The process of the invention is usually conducted as follows. The azetidinonedisulfide compound of the formula (III) is reacted with the compound of the nitrogen-containing heterocyclic compound of the formula (IV) in the presence of a metal compound in a suitable solvent. The nitrogen-containing heterocyclic compound of the formula (IV) is used in an amount of about 2 to 20 moles, preferably about 5 to about 10 moles, per mole of the compound of the azetidinonedisulfide compound of the formula (III). The metal compound is used in an amount of about 1.5 to 5 moles, preferably about 2 to 3 moles per mole of the azetidinonedisulfide compound of the formula (III). The solvent to be used is not particularly limited insofar as it does not adversely affect the reaction and includes, for example, an organic solvent such as acetonitrile, nitromethane, methyl ethyl ketone or the like, and a mixture of such organic solvent and water. The reaction is usually conducted at a temperature of aout 20° to about 100° C., preferably about 50° to about 70° C. The reaction pressure is not critical. The reaction is preferably conducted under atmospheric pressure. It is preferable to conduct the reaction in an atmosphere of an inert gas such as argon gas, nitrogen gas and the like. The reaction is continued until the starting material is consumed and is usually completed within about 0.5 to 24 hours. After the completion of the reaction, the desired compound of the formula (I) can be isolated and purified by a conventional method such as recrystallization, column chromatography and the like.

The compounds of the formula (I) prepared by the process of the invention are useful as intermedeiate for synthesizing the β-lactamase inhibitors of the formula (II). The β-lactamase inhibitor of the formula (II) can be prepared from the compound of the formula (I), for example, by oxidizing the compound of the formula (I). The oxidation reaction is usually conducted in a solvent using a conventional oxidizing agent such as permanganic acid, potassium permanganate, periodic acid, peracetic acid, trifluoroperacetic acd, perbenzoic acid, m-chloroperbenzoic acid, hydrogen peroxide or the like. The oxidizing agent may be used in excess, but may preferably used in an amount of about 1 to 5 moles per mole of the compound of the formula (I). The solvent can be any solvent which does not effect the oxidation reaction and includes dichloromethane, chloroform, carbon tetrachloride, pyridine, tetrahydrofuran, dioxane, acetone, formic acid, dimethylformamide, ethyl acetate, water and the like. The reaction temperature is not particularly limited but generally about 0 to about 60° C.

If desired, the compound of the formula (II) thus prepared may be subjected to a conventional reaction for changing the carboxyl protecting group to a carboxyl protecting group which can be readily metabolized in vivo or to a conventional de-esterification reaction for changing the carboxyl protecting group into a free acid form. Such reactions are described, for example, in "Design of prodrugs", pages 3-6, edited by Hans Bundgaard, 1985, Elsevier Science Publishers B.V. (Biological Division).

The process of the present invention is described in greater detail with reference to the following examples. Reference Example 1 below illustrates the oxidation of the desired compound of the formula (I) to a β-lactamse inhibitor of the formula (II).

EXAMPLE 1

Preparation of p-methoxybenzyl 2α-methyl-2β-(1,2,3-triazol-1-yl)methylpenam-3α-carboxylate To 195 mg of p-methoxybenzyl 3-methyl-2-{2-oxo-4-(benzothiazol-2-yl)dithioazetidin-1-yl}-3-butenoate were added 210 mg of mercury (I) acetate (content 97%), 282 mg of 1H-1,2,3-triazole and 3 ml of acetonitrile, and the mixture was heated with stirring under argon atmosphere at a bath temperature of 70° C. for 6 hours. The reaction mixture was allowed to cool and was filtered on a Celite filter followed by washing the filter with dichloromethane. The resulting filtrate was washed with an aqueous solution of sodium bicarbonate. The organic layer separated was dried over sodium sulfate, and the solvent was evaporated off under reduced pressure. The resulting residue was purified by silica gel column chromatography (eluent: benzene-ethyl acetate=4:1), giving 114.8 mg of p-methoxybenzyl 2α-methyl-2β-(1,2,3-triazol-1-yl)methylpenam-3α-carboxylate as an oil. Yield: 74%.

Infrared absorption spectrum (neat) $\nu_{max}(cm^{-1}) = 1775, 1735$.

Nuclear magnetic resonance spectrum (CDCl$_3$) δ(ppm)=1.34 (3H, s), 3.03, 3.53 (2H, AB-X, J=16 Hz, J=2 Hz, J=4 Hz), 3.78 (3H, s), 4.58 (2H, s), 4.74 (1H, s), 5.09 (2H, s), 5.39 (1H, dd, J=4, 2 Hz), 6.83 (2H, d, J=8 Hz), 7.26 (2H, d, J=8 Hz), 7.68 (2H, m).

EXAMPLE 2

Preparation of p-methoxybenzyl 2α-methyl-2β-(1,2,3-triazol-1-yl)methylpenam-3α-carboxylate To 176 mg of p-methoxybenzyl 3-methyl-2-{2-oxo-4-(pyridin-2-yl)dithioazetidin-1-yl}-3-butenoate were added 219 mg of mercury (I) acetate (content 97%), 282 mg of 1H-1,2,3-triazole and 2 ml of acetonitrile, and the mixture was heated with stirring under argon atmosphere at a bath temperature of 70° C. for 6 hours. The reaction mixture was allowed to cool and was filtered on a Celite filter followed by washing the filter with dichloromethane. The resulting filtrate was washed with an aqueous solution of sodium bicarbonate. The organic layer separated was dried over sodium sulfate, and the solvent was evaporated off under reduced pressure. The resulting residue was purified by silica gel column chromatography (eluent: benzene-ethyl acetate=4:1), giving 78.6 mg of p-methoxybenzyl 2α-methyl-2β-(1,2,3-triazol-1-yl)methylpenam-3α-carboxylate as an oil. Yield: 56%.

The infrared absorption spectra (neat) and nuclear magentic resonance spectra (CDCl$_3$) of the resulting produce were identical with those of the product of Example 1.

EXAMPLES 3–15

Following the generally procedure of Example 1 and using the starting material of the formula (III) and reactant of the formula (IV) listed in Table 1 below, the products of the formula (I) and shown in Table 1 were prepared.

Table 1 shows the yields achieved. Table 2 below shows the spectral data of the products obtained.

EXAMPLES 16–18

Following the general procedure of Example 1 and conducting the reaction in a different solvent listed in Table 3 at a temperature of at 70° C., the product of Example 1 was prepared.

Table 3 shows the yield achieved.

In Tables 1 to 3, the abbreviations used therein have the following meaning.

BT: benzothiazol-2-yl
P: 2-pyridyl
BO: benzoxazol-2-yl
MT: 1-methyl-tetrazol-5-yl
MTD: 5-methyl-1,3,4-thiadiazol-2-yl
PMB: p-methoxybenzyl
PNB: p-nitrobenzyl
Bh: benzhydryl
PM: 2-pyrimidyl
Me: methyl

TABLE 1

| Ex. | Compound (III) | Compound (IV) | Metal compd | Product (I) | Yield (%) |
|---|---|---|---|---|---|
| 3 | (structure with S—SBT, COOPMB) | HN-triazole | HgO | (penam product, COOPMB) | 51 |
| 4 | (structure with S—SBT, COOPMB) | HN-triazole | AgOAc | (penam product, COOPMB) | 51 |
| 5 | (structure with S—SBT, COOBh) | HN-triazole | HgOAc | (penam product, COOBh) | 68 |

TABLE 1-continued

| Ex. | Compound (III) | Compound (IV) | Metal compd | Product (I) | Yield (%) |
|---|---|---|---|---|---|
| 6 | S—S—P structure with COOPNB | HN-triazole | HgOAc | triazole-substituted product | 39 |
| 7 | S—SBT structure with COOPNB | HN-triazole with MeOOC, COOMe | AgOAc | N1-triazole product with COOMe, COOMe, COOPNB | 53 |
|  |  |  |  | N2-triazole product with COOMe, COOMe, COOPNB | 43 |
| 8 | S—SBO structure with COOPNB | HN-triazole with MeOOC, COOMe | AgOAc | N1-triazole product with COOMe, COOMe, COOPNB | 53 |
|  |  |  |  | N2-triazole product with COOMe, COOMe, COOPNB | 35 |
| 9 | S—SMT structure with COOPNB | HN-triazole with COOMe, COOMe | Ce(OAc)₃ | N1-triazole product with COOMe, COOMe, COOPNB | 26 |
|  |  |  |  | N2-triazole product with COOMe, COOMe, COOPNB | 25 |
| 10 | S—S—MTD structure with COOPNB | HN-triazole with MeOOC, COOMe | HgO | N1-triazole product with COOMe, COOMe, COOPNB | 40 |
|  |  |  |  | N2-triazole product with COOMe, COOMe, COOPNB | 40 |

TABLE 1-continued

| Ex. | Compound (III) | Compound (IV) | Metal compd | Product (I) | Yield (%) |
|---|---|---|---|---|---|
| 11 | S—S—PM azetidinone, COOPMB | HN-triazole with MeOOC, COOMe | AgOAc | triazole-substituted product with COOMe, COOMe, COOPMB | 53 |
|  |  |  |  | isomeric triazole product COOMe, COOMe, COOPMB | 41 |
| 12 | S—SBT azetidinone, COOPMB | benzotriazole (1H) | HgOAc | benzotriazolyl product, COOPMB | 46 |
| 13 | S—SBT azetidinone, COOPMB | tetrazole HN | HgOAc | tetrazolyl product, COOPMB | 34 |
|  |  |  |  | isomeric tetrazolyl product, COOPMB | 35 |
| 14 | S—SBT azetidinone, COOPMB | 1,2,4-triazole NH | HgOAc | triazolyl product, COOPMB | 40 |
| 15 | S—SBT azetidinone, COOPNB | imidazole HN | HgOAc | imidazolyl product, COOPNB | 33 |

TABLE 2

| Ex. | Product | IR ($\nu$ cm$^{-1}$) | NMR ($\delta$, ppm) |
|---|---|---|---|
| 3 |  |  | (identical with Example 1) |
| 4 | triazolyl-methyl penem product, COOPMB |  |  |

TABLE 2-continued

| Ex. | Product | IR (νcm⁻¹) | NMR (δ, ppm) |
|---|---|---|---|
| 5 | (structure with pyrazole, COOBh) | 1760, 1740 | 1.28(3H,s),3.13,3.61(2H,AB—X,J=16Hz, J=2Hz,J=4Hz),4.57(2H,s),4.87(1H,s), 5.37(1H,dd,J=2,4Hz),6.87(1H,s), 7.27(10H,s),7.68(1H,s) |
| 6 | (structure with triazole, COOPNB) | 1775, 1740 | 1.40(3H,s),3.20,3.71(2H,AB—X,J=16Hz, J=2Hz,J=4Hz),4.63(2H,s),4.90(1H,s), 5.27(2H,s),5.43(1H,dd,J=2,4Hz), 7.5(2H,d,J=9Hz),7.75(2H,m), 8.25(2H,d,J=9Hz) |
| 7, 8 | (structure with triazole dicarboxylate, COOPNB) | 1785–1735 (broad) | 1.38(3H,s),3.22,3.62(2H,AB—X,J=16Hz, J=2Hz,J=4Hz),3.99(6H,s),4.97(2H,s), 5.18(1H,s),5.28(2H,s),5.37(1H, dd,J=2,4Hz),7.53(2H,d,J=9Hz), 8.23(2H,d,J=9Hz) |
| 9, 10 | (structure with triazole dicarboxylate, COOPNB) | 1775, 1720 | 1.32(3H,s),3.20,3.64(2H,AB—X,J=16Hz, J=2Hz,J=4Hz),3.97(6H,s),4.75(2H,s), 5.23(2H,s),5.35(1H,m),5.40(1H,s), 7.48(2H,d,J=8Hz),8.20(2H,d,J=8Hz) |
| 11 | (structure with triazole dicarboxylate, COOPMB) | 1770, 1735, 1720 | 1.33(3H,s),3.16,3.54(2H,AB—X,J=16Hz, J=2Hz,J=4Hz),3.80(3H,s),3.97(6H,s), 4.92(2H,s),4.98(1H,s),5.12(2H,s), 5.33(1H,dd,J=2,4Hz),6.92(2H,d,J=8Hz), 7.28(2H,d,J=8Hz) |
|  | (structure with triazole dicarboxylate, COOPMB) | 1780, 1740 | 1.28(3H,s),3.15,3.59(2H,AB—X,J=16Hz, J=2Hz,J=4Hz),3.80(3H,s),3.95(6H,s), 4.72(2H,s),5.08(2H,s),5.23(1H,s), 5.32(1H,dd,J=2,4Hz),6.83(2H,d,J=8Hz), 7.23(2H,d,J=8Hz) |
| 12 | (structure with benzotriazole, COOPMB) | 1775, 1740 | 1.38(3H,s),3.20,3.51(2H,AB—X,J=16Hz, J=2Hz,J=4Hz),3.78(3H,s),4.85(2H,s), 4.97(1H,s),5.10(2H,s),5.33(1H, dd,J=2,4Hz),6.82(2H,d,J=8Hz), 7.1–7.7(5H,m),7.9–8.2(1H,m) |
| 13 | (structure with tetrazole, COOPMB) | 1775, 1740 | 1.33(3H,s),3.19,3.61(2H,AB—X,J=16Hz, J=2Hz,J=4Hz),3.82(3H,s),4.62(2H,s), 4.67(1H,s),5.10(2H,s),5.38(1H,dd, J=2,4Hz),6.93(2H,d,J=8Hz),7.23(2H, d,J=8Hz),8.75(1H,s) |
|  | (structure with tetrazole, COOPMB) | 1780, 1742 | 1.25(3H,s),3.15,3.61(2H,AB—X,J=16Hz, J=2Hz,J=4Hz),3.78(3H,s),4.87(2H,s), 5.08(2H,s),5.23(1H,s),5.33(1H,dd, J=2,4Hz),6.82(2H,d,=8Hz), 7.23(2H,d,J=8Hz),8.48(1H,s) |

TABLE 2-continued

| Ex. | Product | IR (νcm⁻¹) | NMR (δ, ppm) |
|---|---|---|---|
| 14 | (penam structure with -N(triazole) CH₂ group, COOPMB ester) | 1770,1735 | 1.32(3H,s),3.14,3.62(2H,AB—X,J=16Hz, J=2Hz,J=4Hz),3.80(3H,s),4.37(2H,s), 4.93(1H,s),5.10(2H,s),5.37(1H,dd, J=2,4Hz),6.85(2H,d,J=8Hz),7.23(2H, d,J=8Hz),7.93(1H,s)8.12(1H,s) |
| 15 | (penam structure with -N(imidazole) CH₂ group, COOPNB ester) | 1773,1750 | 1.37(3H,s),3.13,3.69(2H,AB—X,J=16Hz, J=2Hz,J=4Hz),4.16(2H,s),4.69(1H,s), 5.22(2H,s),5.36(1H,m),7.01(2H,s), 7.45(2H,s),7.51(1H,s),8.16(2H,d) |

TABLE 3

| Ex. | Compound (III) | Solvent | Reaction temp. | Reaction time | Product | Yield (%) |
|---|---|---|---|---|---|---|
| 16 | (S-SBT azetidinone with isopropenyl, COOPMB) | CH₃NO₂ | 70° C. | 6 hr | (penam triazolylmethyl, COOPMB) | 69 |
| 17 | (S-SBT azetidinone with isopropenyl, COOPMB) | CH₃CCH₂CH₃ (with =O) | 70° C. | 3 hr | (penam triazolylmethyl, COOPMB) | 51 |
| 18 | (S-SBT azetidinone with isopropenyl, COOPMB) | CH₃CN—H₂O (3:1) | 70° C. | 3 hr | (penam triazolylmethyl, COOPMB) | 46 |

REFERENCE EXAMPLE 1

Preparation of p-methoxybenzyl 2α-methyl-2β-(1,2,3-triazol-1-yl)methylpenam-3α-carboxylate 1,1-dioxide A 980 mg quantity of p-methoxybenzyl 2α-methyl-2β-(1,2,3-triazol-1-yl)methylpenam-3α-carboxylate was dissolved in a mixture of 6 ml of acetone and 2 ml of water, and 3 ml of acetic acid was added to the solution. Then, 814 mg of potassium permanganate was added with stirring under ice-cooling, and the mixture was stirred at room temperature for 3 hours. After addition of 30% hydrogen peroxide until the reaction mixture became colorless, the mixture was extracted with 50 ml of methylene chloride. The methylene chloride layer was evaporated off and the residue was subjected to a silica gel column chromatography (eluent:chloroform-acetone=19:1), giving 976 mg of the title compound in the form of a foam. Yield: 92%.

Infrared absorption spectrum (KBr) ν$_{max}$ (cm⁻¹)=1800, 1792, 1760.

Nuclear magnetic resonance spectrum (CDCl₃) δ(ppm)=1.20 (3H, s), 3.50–3.55 (2H, m), 3.82 (3H, s), 4.55 (1H, s), 4.59–4.66 (1H, m), 5.03 (2H, s), 5.21 (2H, s), 6.92 (2H, d, J=8.8 Hz), 7.36 (2H, d, J=8.8 Hz), 7.72 (1H, d, J=1.1 Hz), 7.76 (1H, d, J=1.1 Hz).

We claim:

1. A process for preparing a 2β-substituted-methyl-penicillin derivative represented by the formula

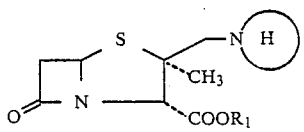

(I)

wherein

is pyrazolyl, imidazolyl, 1,2,3-triazolyl, 1,2,4-triazolyl, tetrazolyl, benzotriazolyl, benzopyrazolyl or benzimidazolyl each of which may have 1 to 3 substituents selected from the class consisting of C₁–C₆ straight- or branched-chain alkyl group, C₁–C₆ straight- or branched-chain alkoxy group, C₂–C₆ acyl group, carbamoyl group, $C_1$–$C_6$ alkyl-substituted carbamoyl group, halogen atom, hydroxy group, trifluoromethyl group, nitro group, amino group, formyl group, $C_1$–$C_6$ alkoxy-$C_1$–$C_6$ alkyl group, $C_2$–$C_7$ alkoxycarbonyl group, $C_3$–$C_7$ alkenyloxycarbonyl group, benzyloxycarbonyl group which may optionally have 1–3 substituents selected from the group consisting of $C_1$–$C_6$ alkyl group, a halogen atom and nitro group on the benzene ring, phenyl group which may optionally have 1–3 substituents selected from the group consisting of $C_1$–$C_6$ alkyl group, $C_1$–$C_6$ alkoxy group and halogen atom on the benzene ring, $C_1$–$C_6$ alkyl groups substituted with 1–3 phenyl groups, $C_1$–$C_6$ alkylthio group, $C_1$–$C_6$ alkylsulfinyl group and $C_1$–$C_6$ alkylsulfonyl group, and $R_1$ is a penicillin carboxyl protecting group selected from the group consisting of methyl, ethyl, propyl, butyl, tert-butyl, 1,1-dimethylpropyl, 1-cyclopropylmethyl, 2-cyano-1,1-dimethylethyl, bromobenzoylmethyl, p-nitrobenzoylmethyl, dimethylaminomethyl, methylthiomethyl, phenylthiomethyl, succinimidomethyl, trichloroethyl, tribromoethyl, 1,1-dimethyl-2-propenyl, 1,3-dimethyl-3-butenyl, benzyl, diphenylmethyl, trityl, p-nitrobenzyl, p-methoxybenzyl, di(p-methoxyphenyl)methyl, acetoxymethyl, acetoxyethyl, propionyloxyethyl, pivaloyloxymethyl, pivalolyloxyethyl, pivaloyloxypropyl, benzoyloxymethyl, benzoyloxyethyl, benzylcarbonyloxymethyl, cyclohexylcarbonyloxymethyl, methoxymethyl, ethoxymethyl, benzyloxymethyl, 3-phthalidyl, crotonolacton-4-yl, tetrahydropyranyl, dimethylchlorosilyl, trichlorosilyl, pyridine-1-oxide-2-methyl and quinoline-1-oxide-2-methyl, which comprises reacting an azetidinonedisulfide compound of the formula

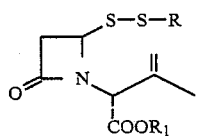

wherein $R_1$ is as defined above, and R is a 5- or 6-membered heterocyclic group, which contains 1 to 4 nitrogen atoms and may further contain one oxygen or sulfur atom as the heteroatom in the ring structure, and which may optionally be fused with a benzene ring, and which may optionally have 1 to 3 substituents, selected from the group consisting of $C_1$–$C_4$ alkyl, $C_1$–$C_4$ alkoxy halogen atom, nitro, phenyl, tolyl, xylyl, benzyl, phenethyl and trityl, with a nitrogen-containing heterocyclic compound of the formula

H—N Y (IV)

wherein

is as defined above, in a solvent and in the presence of a metal compound which is an organic carboxylic acid salt, carbonate or oxide of silver, mercury, cerium, copper, lead or thallium, wherein the metal compound is used in an amount of about 1.5 to 5 moles per mole of the compound of the formula (III), the compound of the formula (IV) is used in an amount of about 2 to 20 moles per mole of the compound of the formula (III), and the reaction is carried out at a temperature of about 20° to 100° C.

2. A process as defined in claim 1 wherein

is pyrazol-1-yl, imidazol-1-yl, 1,2,3-triazol-1-yl-, 1,2,3-triazol-2-yl, 1,2,4-triazol-1-yl, 1,2,4-triazol-4-yl, tetrazol-1-yl, tetrazol-2-yl, benzotriazol-1-yl, benzpyrazol-1-yl or benzimidazol-1-yl, each of which may have 1 to 3 substituents selected from the class consisting of $C_1$–$C_6$ straight- or branched-chain alkyl group, $C_1$–$C_6$ straight- or branched-chain alkoxy group, $C_2$–$C_6$ acyl group, carbamoyl group, $C_1$–$C_6$ alkyl-substituted carbamoyl group, halogen atom, hydroxyl group, trifluoromethyl group, nitro group, amino group, formyl group, $C_1$–$C_6$ alkoxy-$C_1$–$C_6$ alkyl group, $C_2$–$C_7$ alkoxycarbonyl group, $C_3$–$C_7$ alkenyloxycarbonyl group, benzyloxycarbonyl group which may have 1–3 substituents selected from the group consisting of $C_1$–$C_6$ alkyl group, a halogen atom and nitro group on the benzene ring, phenyl group which may optionally have 1–3 substituents selected from the group consisting of $C_1$–$C_6$ alkyl group, $C_1$–$C_6$ alkoxy group and halogen atom on the benzene ring, $C_1$–$C_6$ alkyl group, $C_1$–$C_6$ alkoxy group and halogen atom on the benzene ring, $C_1$–$C_6$ alkyl groups substituted with 1–3 phenyl groups, $C_1$–$C_6$ alkylthio group, $C_1$–$C_6$ alkylsulfinyl group and $C_1$–$C_6$ alkylsulfonyl group.

3. A process as defined in claim 1 wherein R is benzothiazol-2-yl, 2-quinolyl, 2-pyridyl, 3-pyridyl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 1-methylimidazol-2-yl, 1-methylbenzimidazol-2-yl, benzoxazol-2-yl, 1-methyltetrazol-5-yl, 5-methyl-1,3,4-thiadiazol-2-yl or 4-methylthiazol-2-yl.

4. A process as defined in claim 1, wherein the metal compound is an acetic acid salt, carbonate or oxide of silver, mercury or cerium.

5. A process as defined in claim 4, wherein the metal compound is mercury oxide, mercury acetate or cerium acetate.

6. A process as defined in claim 1 wherein the metal compound is used in an amount of about 2 to 3 moles per mole of the compound of the formula (III).

7. A process as defined in claim 1 wherein the compound of the formula (IV) is used in an amount of about 5 to 10 moles per mole of the compound of the formula (III).

8. A process as defined in claim 1 wherein the reaction is carried out at a temperature of about 50° to 70° C.

9. A process as defined in claim 1 wherein the compound of the formula (IV) is used in an amount of about 2 to about 10 moles per mole of the compound of the formula (III).

* * * * *

UNITED STATES PATENT AND TRADEMARK OFFICE
CERTIFICATE OF CORRECTION

PATENT NO. : 4,898,939

DATED : February 6, 1990

INVENTOR(S) : Sigeru TORII et al.

It is certified that error appears in the above-identified patent and that said Letters Patent is hereby corrected as shown below:

In the Abstract, delete " 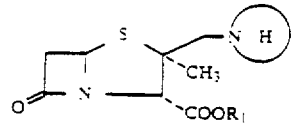 "

and substitute therefor --

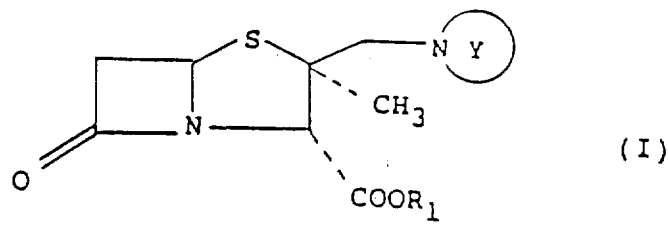 --.

Column 16, line 50, delete " 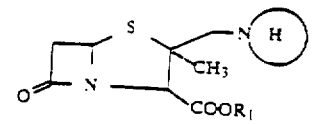 "

and substitute therefor --

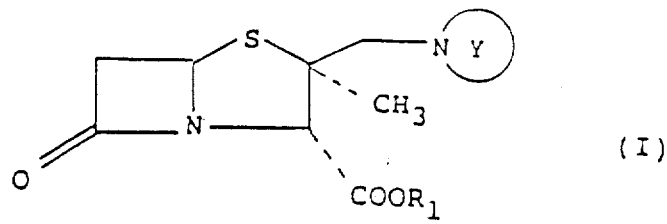 --.

UNITED STATES PATENT AND TRADEMARK OFFICE
CERTIFICATE OF CORRECTION

PATENT NO. : 4,898,939

DATED : February 6, 1990

INVENTOR(S) : Sigeru TORII et al.

It is certified that error appears in the above-identified patent and that said Letters Patent is hereby corrected as shown below:

Column 17, line 50, after "alkoxy" insert --,--.

line 54, delete " $H-N\ Y$ " $(IV)$ and substitute therefor --

$H-N\underset{\phantom{x}}{\overset{\frown}{\;Y\;}}$ $(IV)$ --.

UNITED STATES PATENT AND TRADEMARK OFFICE
CERTIFICATE OF CORRECTION

PATENT NO. : 4,898,939

DATED : February 6, 1990

INVENTOR(S) : Sigeru TORII, et al

It is certified that error appears in the above-identified patent and that said Letters Patent is hereby corrected as shown below:

Column 18, line 10, delete " . —N Y "

and substitute therefor -- -N(Y) --.

Signed and Sealed this

Twelfth Day of May, 1992

Attest:

DOUGLAS B. COMER

*Attesting Officer*     *Acting Commissioner of Patents and Trademarks*